US005803087A

United States Patent [19]
Thompson

[11] Patent Number: 5,803,087
[45] Date of Patent: Sep. 8, 1998

[54] BACKBOARD IMMOBILIZATION DEVICE

[76] Inventor: Jason A. Thompson, 7208 Terrell La., Hampton, Va. 23666

[21] Appl. No.: 908,343

[22] Filed: Aug. 7, 1997

[51] Int. Cl.[6] ........ A61F 5/37
[52] U.S. Cl. ........ 128/870; 5/627; 5/628
[58] Field of Search ........ 128/845, 846, 128/869, 870, 876; 5/625, 627, 628

[56] References Cited

U.S. PATENT DOCUMENTS

| | | | |
|---|---|---|---|
| 713,405 | 11/1902 | Crawford . | |
| 795,524 | 7/1905 | Leffmann . | |
| 1,326,931 | 1/1920 | Himes . | |
| 1,795,435 | 3/1931 | Melzer | 5/627 |
| 2,242,311 | 5/1941 | Lucey . | |
| 2,417,378 | 3/1947 | Robinson . | |
| 2,503,314 | 4/1950 | Atwood | 5/628 |
| 2,708,276 | 5/1955 | Schloss | 5/627 |
| 3,125,766 | 3/1964 | Halperin . | |
| 3,574,871 | 4/1971 | Greene | 5/628 |
| 3,597,773 | 8/1971 | Firestone . | |
| 3,653,079 | 4/1972 | Bourgraf et al. . | |
| 3,801,208 | 4/1974 | Bourgraf et al. . | |
| 3,921,231 | 11/1975 | Bourgraf et al. . | |
| 4,480,345 | 11/1984 | Dunn . | |
| 5,109,555 | 5/1992 | Fickler | 5/627 |

FOREIGN PATENT DOCUMENTS

| | | |
|---|---|---|
| 296279 | 8/1928 | United Kingdom . |

OTHER PUBLICATIONS

FERNO, “Model 65 Scoop Stretcher”, User’s Manual, May 1996, pp. 1–7, USA.

Hartwell Medical, Advertisement, *Journal of Emergency Medical Services*, Mar. 1997, vol. 22, No. 3, USA.

*Primary Examiner*—Michael A. Brown
*Attorney, Agent, or Firm*—Joy L. Bryant

[57] ABSTRACT

A backboard immobilization device is provided. The device includes first and second complimentary body support panels which are detachably interconnected at each end by a lock. Each lock has a first tube and a second tube. The first tube has a first end disposed within the first body support panel and a second end extending therefrom. The second end is tapered and has a locking pin. The second tube has a first end disposed within the second body support panel and a second end extending therefrom. The second end has a retracting sleeve wherein the retracting sleeve is slidably connected to the tapered end of the first tube and interlocks with the locking pin.

8 Claims, 4 Drawing Sheets

BACKBOARD IMMOBILIZATION DEVICE

FIELD OF THE INVENTION

The present invention relates to backboard immobilization devices. In particular, it relates to backboard immobilization devices having complimentary body support panels and a lock having a rotating sleeve and a locking pin.

BACKGROUND OF THE INVENTION

Emergency medical personnel have found it to be desirable to immobilize a patient before removing him from the scene of the accident without having to lift, twist, turn or roll the patient onto the immobilization device. Break-away or splint-stretchers have been found to be suitable for accomplishing such a task.

Robinson in U.S. Pat. No. 2,417,378 discloses a body supporting frame having a pair of rigid, elongate side members pivotally connected at one end and separably connected at the opposite end thereof, so that the frame may be applied beneath a body by spreading or obliquely diverging its hinged sides, then closing or converging them beneath the torso along the lines of cleavage between the body and the ground or bed on which it lies, and finally locking the sides in parallel relation, without lifting, turning or rolling the body.

Halperin in U.S. Pat. No. 3,125,766 improved on Robinson's invention in that he provided a splint-stretcher having extruded aluminum side frames which are normally spaced apart when the stretcher is closed, in order to support the sides of the torso without exerting pressure on the spine. The side frames have wide and relatively thin body supporting surfaces of mutually converging inclination, and integral underlying, hollow ribs of greater thickness, adapted to support the stretcher when placed on the ground or floor, to provide skids on which the loaded stretcher may be slid over a surface. Tubular channels are provided for receiving the telescoping rods of extensible, lengthwise adjustable, leg-supporting portions of the side frames; and which are fixedly connected to cast aluminum. In addition, transverse hand grips or bars are positioned at the outer ends of the frame, the free ends of each pair of hand grips being pivotally connectable and at least one of the pivotal connections is readily separable.

Bourgraf et al. in U.S. Pat. No. 3,653,079 further improve on the break-away splint stretcher by providing a stretcher which is both readily adjustable and capable of being folded to conserve space. The opposing halves of the stretcher are connected together by readily releasable pivot locks which are fail-safe, together with fail-safe locking hinges for the foldable part of the stretcher. The stretcher has a tubular frame mounting body supporting panels. The frame being provided at its opposite ends with pivot locks which are selectively disengageable to permit the opposite halves of the stretcher frame to be pivoted outwardly about the other pivot lock. The stretcher frame also is provided with an extensible leg supporting section and/or a folding head supporting section mounted on the frame by locking hinges. The pivot locks and the locking hinges each are provided with finger actuated release means arranged to prevent accidental disengagement of the parts.

Bourgraf et al. further describe the pivot locking means in U.S. Pat. No. 3,801,208. The pivot lock has opposite parts one of which is bifurcated and mounts a pivot pin. The other part is in the form of a tongue having a pin receiving slot therein together with a pin engaging latch member adapted to releasably maintain the pin in the slot.

Bourgraf et al in U.S. Pat. No. 3,921,231 disclose a device for extracting a victim from the wreckage in the body position in which the victim was found. Such a device may be fitted to the injured person even though the 30 person is found in a seated or fetal position. The parts of the stretcher are separable and capable of being fitted about the patient in the condition encountered. Thus the stretcher serves a dual function of an extrication device as well as a means for immobilizing and transporting the patient. This device is composed of three frame sections, namely, a head and back section adapted to be connected to either a lower torso and leg section or to a seat section, depending upon the nature of the injuries encountered. Each of the frame sections is composed of complimentary frame parts preferably formed from aluminum tubing which mount supporting panels or scoops for the various parts of the body being supported, such supports preferably being formed from aluminum ribs covered with aluminum sheeting. Each set of complimentary frame parts is connected together at one end by means of a pivot lock such as that disclosed in U.S. Pat. No. 3,801,208.

Dunn in U.S. Pat. No. 4,480,345 improves on the break-away stretcher disclosed in U.S. Pat. No. 3,653,079. He discloses that difficulties have been experienced in maintaining proper alignment between the patient supporting panels of the extensible section and those of the body section. This is due to the fact that when the opposing sides of the stretcher are disconnected, the tubular leg members of the extensible frame section are free to rotate relative to each other, such rotation resulting in misalignment of the patient supporting panels. The problem is magnified by the use of locking pins to secure the leg section, rotation of the leg members also resulting in lateral misalignment of the locking pins with respect to the openings in which they are to be received. To overcome this difficulty, Dunn provided an improved stretcher wherein the telescoping frame members, while movable axially relative to each other, cannot be rotated so as to misalign the support panels; and if locking pins are used, misalignment of the locking pins relative to the opening in which they are adapted to be received is also prevented. The pivot locks of Dunn's invention are those described in U.S. Pat. No. 3,653,079 and U.S. Pat. No. 3,801,208.

Upon use in the field, such pivot locks have proved to be cumbersome to use as well as a pinch hazard to emergency medical personnel. When separating the end couplings, the lock lever button must be depressed and the two halves of the stretcher pulled apart. It has been found that when the emergency medical personnel depress the lock lever button, their fingers get pinched. In turn, such a lock is difficult to operate when wearing latex gloves. In addition, when one lock is left engaged at one end and the stretcher is used in its "V" shaped configuration, caution must be exercised during the application of the stretcher to avoid pinching or pulling the patient's skin, hair or clothing. Lastly, because the stretcher has many moving parts, lubrication is necessary. Failure to wipe off any excess lubricant before returning the stretcher to service results in an increased risk in contamination.

An object of the present invention is to provide a backboard immobilization device which does not require a pivot lock.

Another object of the present invention is to provide a backboard immobilization device which does not require lubrication.

Another object of the present invention is to provide a backboard immobilization device which does not have any pinch points.

These and other objects were achieved by the present invention.

SUMMARY OF THE INVENTION

By the present invention, a backboard immobilization device is provided. The device has first and second complimentary body support panels which are detachably interconnected at each end by a lock. The lock comprises a first tube and a second tube. The first tube has a first end disposed within the first body support panel and a second end extending therefrom. The second end has a tapered end and a locking pin. The second tube has a first end disposed within the second body support panel and a second end extending therefrom. The second end has a retracting sleeve. The retracting sleeve is slidably connected to the tapered end of the first tube and interlocks with the locking pin on the first tube.

Since the lock has no pivot points or screw threads, the possibility of misalignment is significantly reduced. In addition, the tapered end allows the first tube to be easily mated with the second tube having the rotating sleeve. All operational parts of the lock are positioned such that they are lifted up and away from the ground. Thus, the chance of incorporating gravel or grit into the lock during operation is eliminated. The locking pin on the tapered end ensures that the lock is properly engaged where the retracting sleeve eliminates all pinch points and allows for easy operation while wearing gloves.

DETAILED DESCRIPTION OF THE INVENTION

Figure 1:
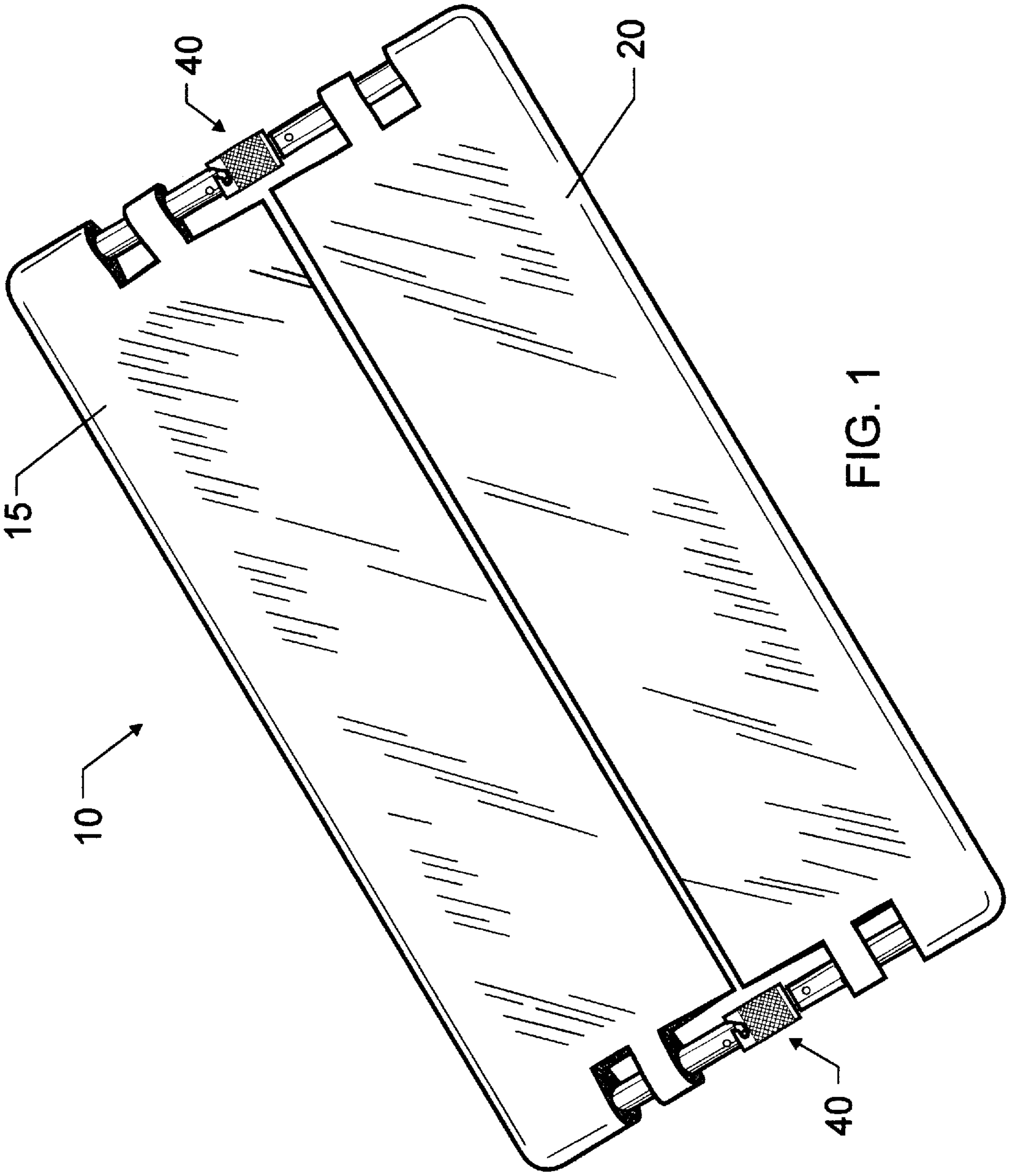
FIG. 1 is an orthographic view of the backboard immobilization device in its assembled position.
Figure 2:
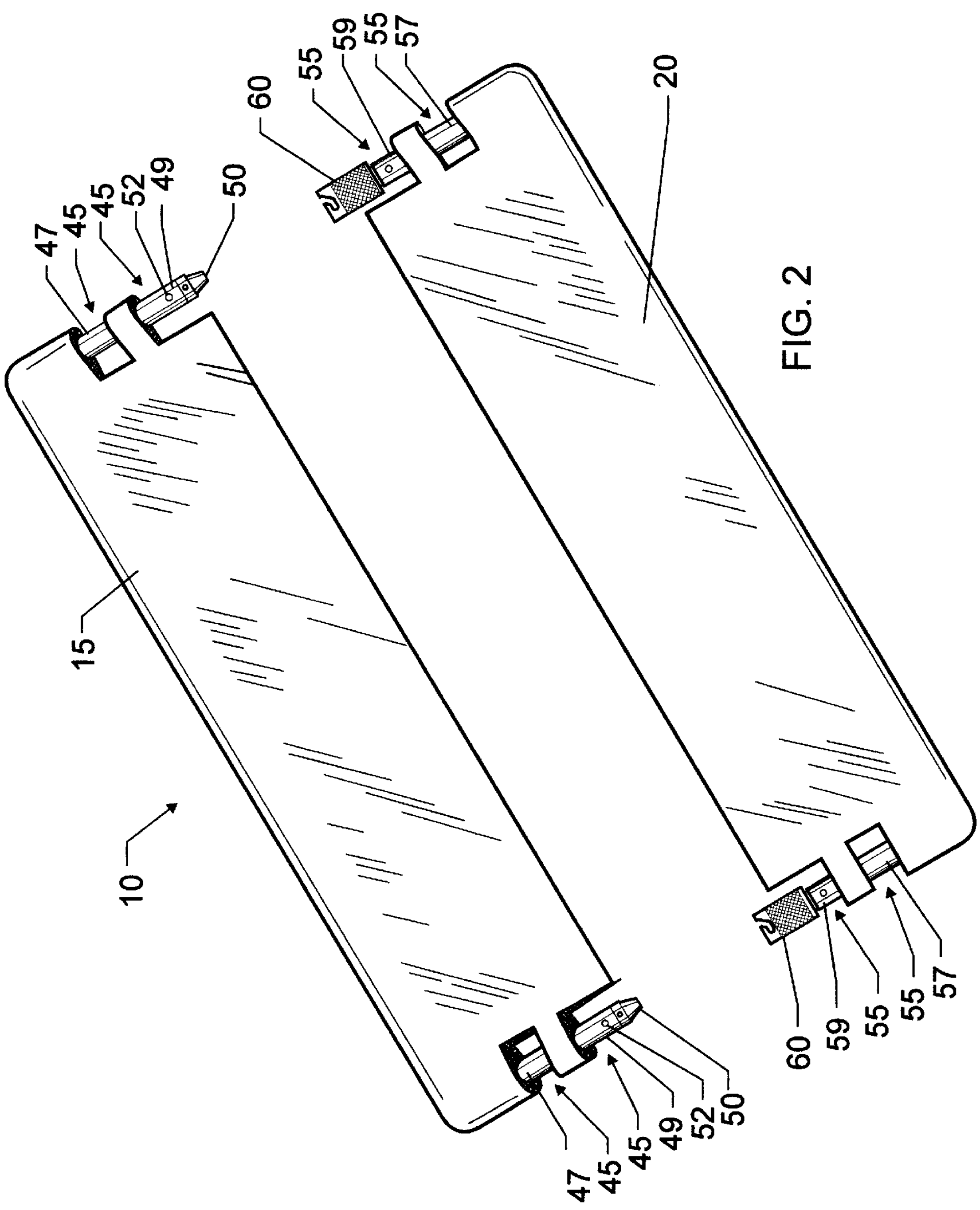
FIG. 2 is an orthographic view of the backboard immobilization device in its unassembled position.

Referring now to FIGS. 1 and 2 where the backboard immobilization device 10 is shown in its assembled and unassembled positions. The backboard immobilization device 10 comprises complimentary first 15 and second 20 body support panels. Each body support panel 15, 20 is preferably prepared from a radiograph transparent material such as a plastic or a reinforced plastic. This allows the patient to undergo radiology without being removed from the immobilization device. Moreover, the choice of a plastic or reinforced plastic material allows for easy and consistent fabrication of each body support panel using any method known to those skilled in the art, and in particular, standard molding or lay-up processes are suitable. This type of fabrication eliminates moving parts and thus the need for periodic lubrication. In turn, the risk of having residual lubrication left on the immobilization device is eliminated.

Each pair of body support panels 15, 20 are complimentary and thus they must be of complimentary lengths and widths. For example, each body support panel has a length ranging from about six feet to about eight feet and, more particularly, a standard length of about seventy-eight inches is acceptable. The width of each panel ranges from about twelve inches to about twenty-one inches and a width of about sixteen inches is desirable. Each body support panel 15, 20 tapers inwardly and is contoured to fit beneath a patient such that no lifting or rolling is required. When the complimentary body support panels 15, 20 are in their assembled position as shown in FIG. 1, a small gap occurs between the two panels. This gap does not exceed a width of about one-half inch.

Figure 3:
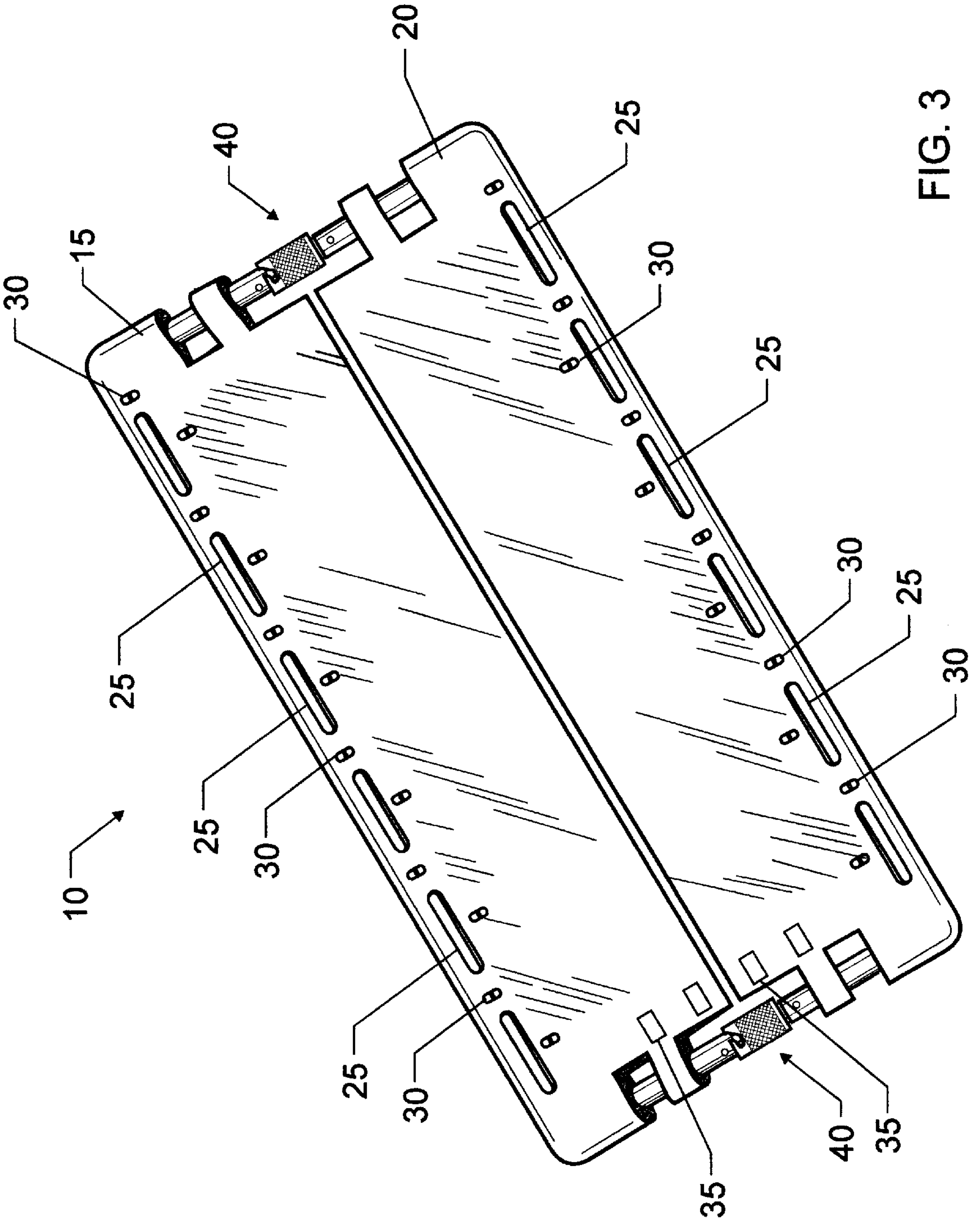
FIG. 3 is an orthographic view of the preferred embodiment of the present invention in its assembled position.

Each body support panel may be modified to provide additional features and benefits as shown in FIG. 3. For example, a plurality of spaced apart handholds 25 are disposed along the outer perimeter of each body support panel 15, 20. The handholds 25 are symmetrically spaced about the perimeter of the immobilization device 10. The handholds 25 may also be ergonomically shaped to allow for easier gripping of the device. In addition to the handholds, a plurality of clip pegs 30 are also disposed within each support panel 15, 20. These clip pegs 30 allow for the attachment of additional straps for immobilizing the patient or for the use of additional emergency medical equipment. Lastly, attachment sites for hook and loop tape 35 may also be added. These sites 35 allow for further immobilization of the patient when such devices as a collar are used.

Referring back to FIG. 1, the first 15 and second 20 complimentary body support panels are detachably interconnected at each end by a lock 40. FIG. 2 shows that the lock comprises a first tube 45 having a first end 47 disposed within the first body support panel 15. This end 47 has either a straight entry into the body support panel or is elongated such that it follows the outer perimeter of the panel around the curve at each end. The second end 49 is tapered 50 and has a locking pin 52. The lock further comprises a second tube 55 having a first end 57 disposed within the second body support panel 20 and a second end 59 extending therefrom. The second end 59 has a retracting sleeve 60. This lock is commercially available from Avibank Corporation and is sold as a tapered lock with an integrated auto-lock mechanism and retracting sleeve design.

Figure 4:
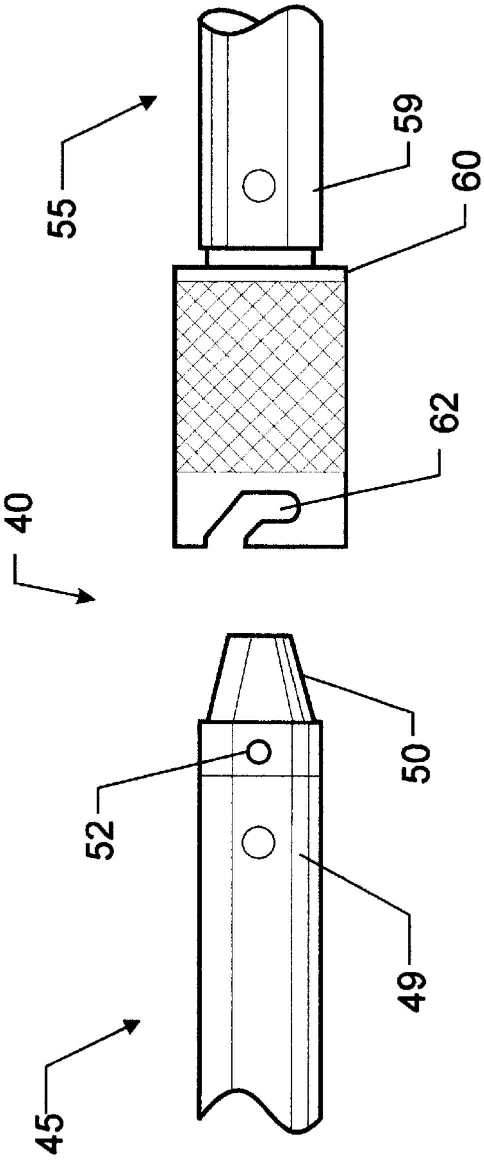
FIG. 4 is a perspective view of the lock of the present invention in its locked position.
Figure 5:
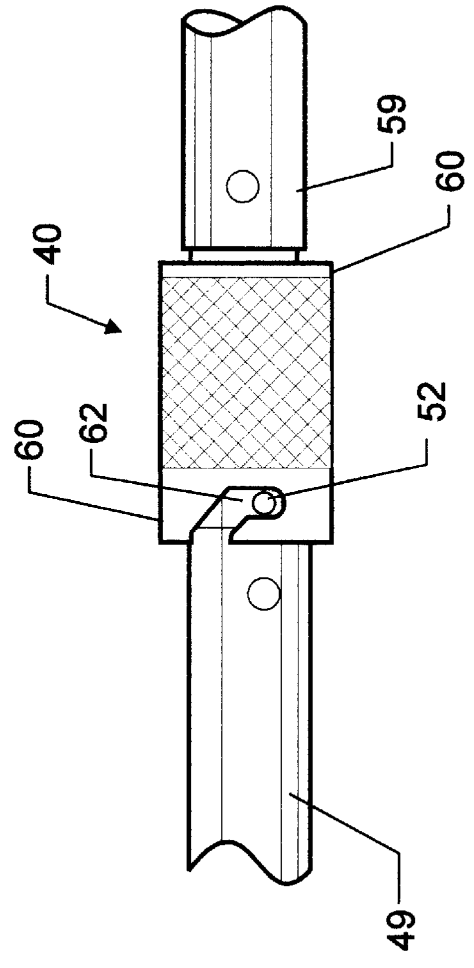
FIG. 5 is a perspective view of the lock of the present invention in its unlocked position.

FIGS. 4 and 5 depict how the lock operates. FIG. 4 shows the open configuration of the lock 40 where FIG. 5 shows the locked configuration. More specifically, the figures show that the second end 49 of the first tube 45 has a tapered end 50 and a locking pin 52 with no screw threads. The second end 59 of the second tube 55 is shown having a retracting sleeve 60 which further has an interlocking groove 62 and no screw threads. When in use, the retracting sleeve 60 is slidably connected or slides into the tapered end 50 of the first tube 45 and the interlocking groove 62 on the retracting sleeve 60 interlocks with the locking pin 52 on the first tube 45. Use of this lock affords many advantages over the prior art. In particular, the shortcomings of the pivot lock are overcome in that the pinch points are eliminated.

What is claimed is:

1. A backboard immobilization device comprising:

first and second complimentary body support panels detachably interconnected at each end by a lock, wherein each lock comprises a first tube and a second tube;

the first tube having a first end disposed within the first body support panel and a second end extending therefrom wherein the second end is tapered and has a locking pin; and wherein the second tube has a first end disposed within the second body support panel and a second end extending therefrom wherein the second end has a retracting sleeve wherein the retracting sleeve is slidably connected to the tapered end of the first tube and interlocks with the locking pin on the first tube.

2. A backboard immobilization device according to claim 1, wherein each complimentary body support panel comprises a radiograph transparent material.

3. A backboard immobilization device according to claim 2, wherein the radiograph transparent material is selected from the group consisting of: a plastic and a reinforced plastic.

4. A backboard immobilization device according to claim 1, wherein each complementary body support panel has a plurality of spaced apart handholds disposed therein.

5. A backboard immobilization device according to claim 4, wherein the handholds are symmetrically spaced.

6. A backboard immobilization device according to claim 1, wherein each complementary body support panel has a plurality of clip pegs disposed therein.

7. A backboard immobilization device according to claim 1, wherein each body support panel has a length ranging from about six feet to about eight feet and a width ranging from about twelve inches to about twenty-one inches; and wherein each body support panel tapers inwardly and is contoured to fit beneath a patient.

8. A backboard immobilization device comprising:

first and second complimentary plastic body support panels, each body support panel has a length ranging from about six feet to about eight feet and a width ranging from about twelve inches to about twenty-one inches, each body support panel tapers inwardly and is contoured to fit beneath a patient; and wherein each body support panel has a plurality of symmetrically spaced apart handholds and a plurality of clip pegs disposed therein; and wherein each body support panel is detachably interconnected at each end with a lock, wherein each lock comprises a first tube and a second tube; the first tube having a first end disposed within the first body support panel and a second end extending therefrom wherein the second end is tapered and has a locking pin; and wherein the second tube has a first end disposed within the second body support panel and a second end extending therefrom wherein the second end has a retracting sleeve, wherein the retracting sleeve is slidably connected to the tapered end of the first tube and interlocks with the locking pin.

* * * * *